United States Patent [19]

Gray

[11] Patent Number: 4,813,413

[45] Date of Patent: Mar. 21, 1989

[54] SURGICAL INSTRUMENT WITH DETACHABLE TOOL MEMBER

[76] Inventor: Frank B. Gray, 5104 Lyons View Dr., Knoxville, Tenn. 37919

[21] Appl. No.: 55,029

[22] Filed: May 28, 1987

[51] Int. Cl.[4] .............................................. A61B 17/00
[52] U.S. Cl. ................................... 128/303 R; 81/423
[58] Field of Search ................... 128/354, 321, 303 R, 128/304, 305; 81/421, 423; 269/259

[56] References Cited

U.S. PATENT DOCUMENTS

| | | | |
|---|---|---|---|
| 2,312,869 | 3/1943 | Boyer | 145/52 |
| 3,039,340 | 6/1962 | Livermont | 81/177 |
| 4,473,070 | 9/1984 | Matthews et al. | 128/305 X |

*Primary Examiner*—Michael H. Thaler
*Attorney, Agent, or Firm*—Pitts and Brittian

[57] ABSTRACT

An improved surgical instrument with detachable tool member (10). The surgical instrument (10) comprises at least one tool member (14) defining a work portion (15) and a rearward end portion (16). The rearward end portion (16) is provided with a tenon (28) for detachably mounting the tool member (14), the tenon (28) defining a narrowed waist portion (34) and an expanded portion (36) rearward of the waist portion (34). The tool member (14) is also provided with a locking rod receptor (42) defining an opening in the rearward end portion (16). The surgical instrument (10) also comprises a tool support member, which in alternate embodiments defines a handle (12) and flexible shaft (48) having a flexible shaft (49). The tool support member includes an outboard end portion (32) provided with a mortise (30) for closely receiving the tenon (28) of the tool member (14) and is further provided with a locking rod passageway (40) defining an opening in the outboard end portion (32) registering with the receptor (42) of the tool member (18). In order to prohibit the tenon (28) from moving laterally within the mortise (30), an elongated locking rod (38) is slidably received in the passageway (40) and in the receptor (42), thereby securing the tenson (28) in the mortise (30).

18 Claims, 5 Drawing Sheets

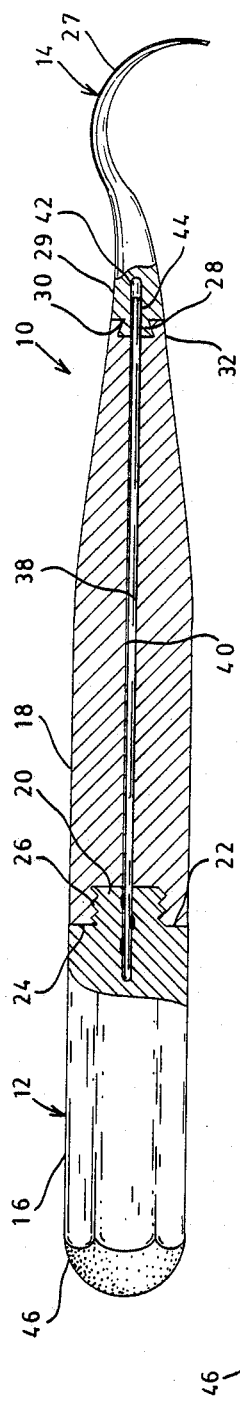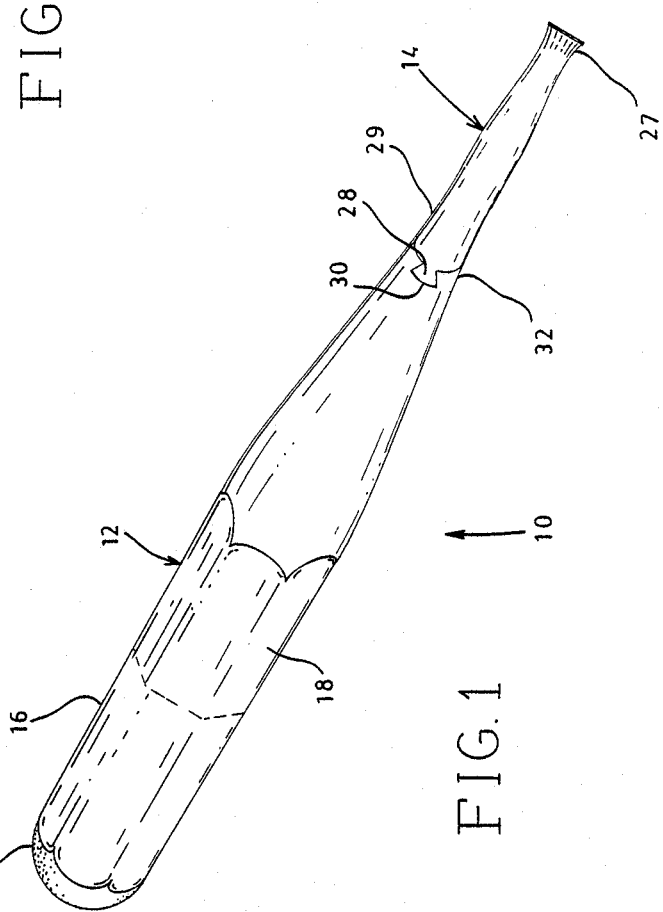

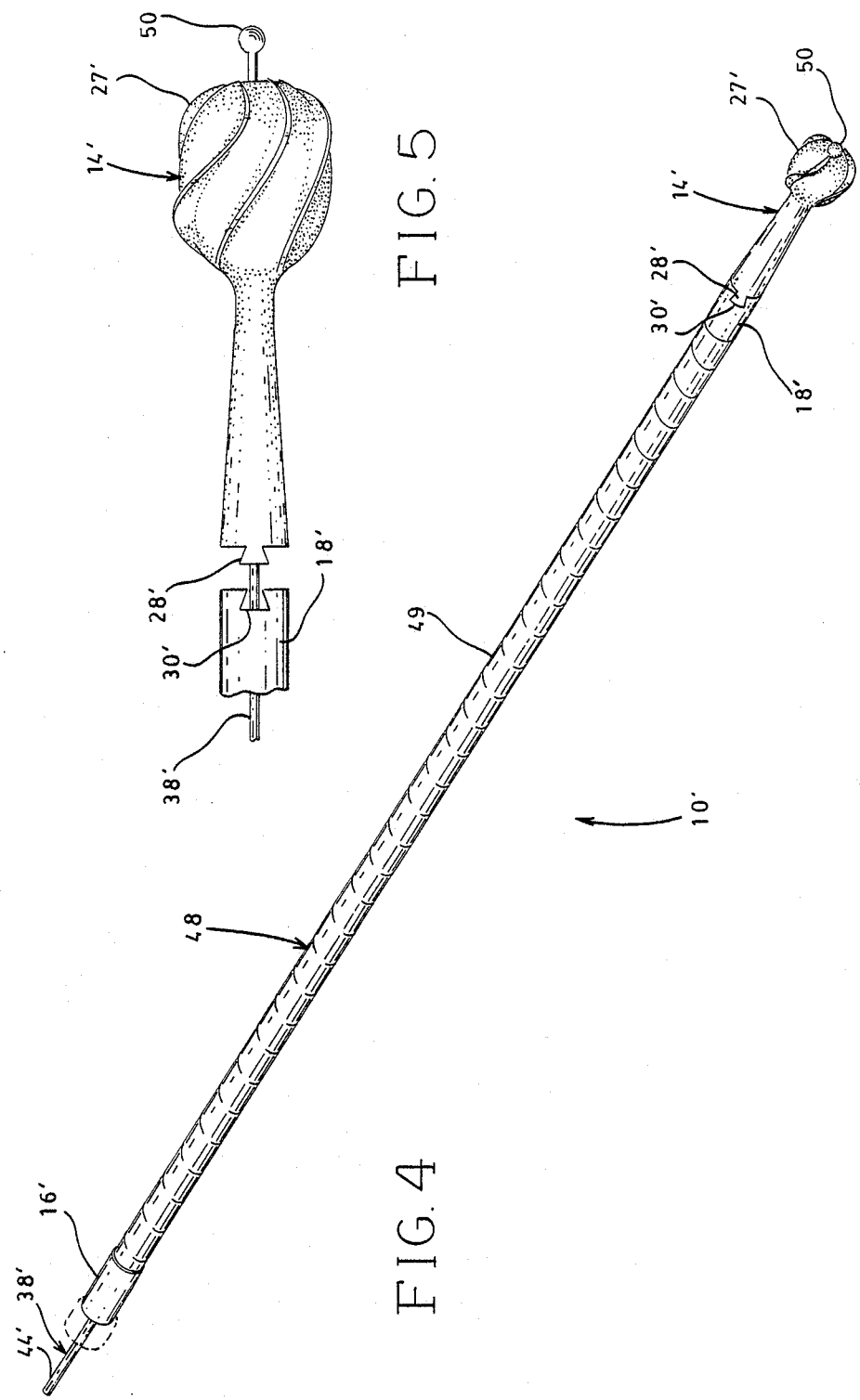

SURGICAL INSTRUMENT WITH DETACHABLE TOOL MEMBER

DESCRIPTION

1. Technical Field

This invention relates to an improved surgical instrument with a detachable tool member. In this particular invention, the surgical instrument includes a tool support member, such as a handle, and at least one tool member which can be releasably mounted on the tool support member.

2. Background Art

Heretofore, surgical instruments such as osteotomes, curets, gouges, scalpels and the like, have comprised handles or tool support members integrally carrying a work implement or tool portion. Because such instruments have been integrally formed, when the tool portion becomes worn or dull through use, the entire instrument must be discarded, or, if possible, taken out of use to be sharpened or otherwise reconditioned. Of course, replacement and/or reconditioning of such instruments can be extremely costly. Certain tools used outside of the medical field, such as wrenches, have been devised which have tool portions which are detachable from the tool handle such that not only can the tool portions be replaced when worn or damaged, but they can be interchanged to provide a tool for multiple tasks. Examples of such tools are disclosed in U.S. Pat. Nos.: 1,006,661, issued to M. A. Knapp on Oct. 24, 1911; 1,413,101, issued to S. J. Cushing on Apr. 18, 1922; 2,231,252, issued to W. L. Chesterman on Feb. 11, 1941; 2,832,246, issued to F. W. Livermont on Apr. 29, 1958; 2,832,943, issued to M. Cutler on Apr. 29, 1958; and 3,039,340, issued to F. W. Livermont on June 19, 1962. However, the coupling means utilized by such devices to releasably secure the tool portions are not readily adaptable to use with surgical instruments. In this regard, most surgical instruments are relatively small in size, and the coupling means must be capable of being scaled accordingly, and yet produce a strong and durable coupling. Further, the coupling means must be such that the tool portions can be quickly interchanged without other tools being necessary to couple and uncouple the tool portions.

Therefore, it is an object of the present invention to provide a surgical instrument with detachable tool members.

A further object of the present invention is to provide an improved surgical instrument which allows a plurality of types of tool members to be detachably mounted on the same support member or handle.

Yet another object of the present invention is to provide an improved surgical instrument with means for detachably securing a tool member which allows tool members to be quickly mounted and/or detached as desired.

Still another object of the present invention is to provide a medical tool with a detachable tool member which is inexpensive to manufacture and avoids the cost of discarding an entire instrument simply because the tool portion has been damaged.

DISCLOSURE OF THE INVENTION

Other objects and advantages will be accomplished by the present invention which provides an improved surgical instrument with detachable tool member. The surgical instrument comprises at least one tool member defining a work portion and a rearward end portion. The rearward end portion is provided with a tenon for detachably mounting the tool member, the tenon defining a narrowed waist portion and an expanded portion rearward of the waist portion. The tool member is also provided with a locking rod receptor defining an opening in the rearward end portion of the tool member. The surgical instrument further comprises a tool support member, which in alternate embodiments defines a handle or a flexible shaft. The tool support member includes an outboard end portion provided with a mortise for closely receiving the tenon of the tool member and is further provided with a locking rod passageway defining an opening in the outboard end portion of the tool support member registering with the rod receptor of the tool member. In order to prohibit the tenon from moving laterally within the mortise, an elongated locking rod is slidably received in the passageway of the tool support member and in the rod receptor of the tool member, thereby securing the tool member on the tool support member.

BRIEF DESCRIPTION OF THE DRAWINGS

The above-mentioned features of the present invention will become more clearly understood from the following detailed description of the invention read together with the drawings in which:

FIG. 1 illustrates a perspective view of an improved surgical instrument of the present invention.

FIG. 2 illustrates a side elevation view, partially in section, of an improved surgical instrument of the present invention.

FIG. 4 illustrates a perspective view of an alternate embodiment of an improved surgical instrument of the present invention.

FIG. 5 illustrates a partial side elevation view of an alternate embodiment of an improved surgical instrument of the present invention.

BEST MODE FOR CARRYING OUT THE INVENTION

An improved surgical instrument with detachable tool member is illustrated at 10 in the figures. The instrument 10 generally comprises a tool support member, which in the preferred illustrated embodiment of the FIGS. 1 through 3 defines a handle 12, and one or more detachable tool members 14. Of course, it will be understood that whereas only two different tool implements are depicted in the figures, the tool members 14 can define various medical/surgical tools, including without limitation osteotomes, chisels, curets, gouges, grasps, scalpels and the like.

Figure 3:
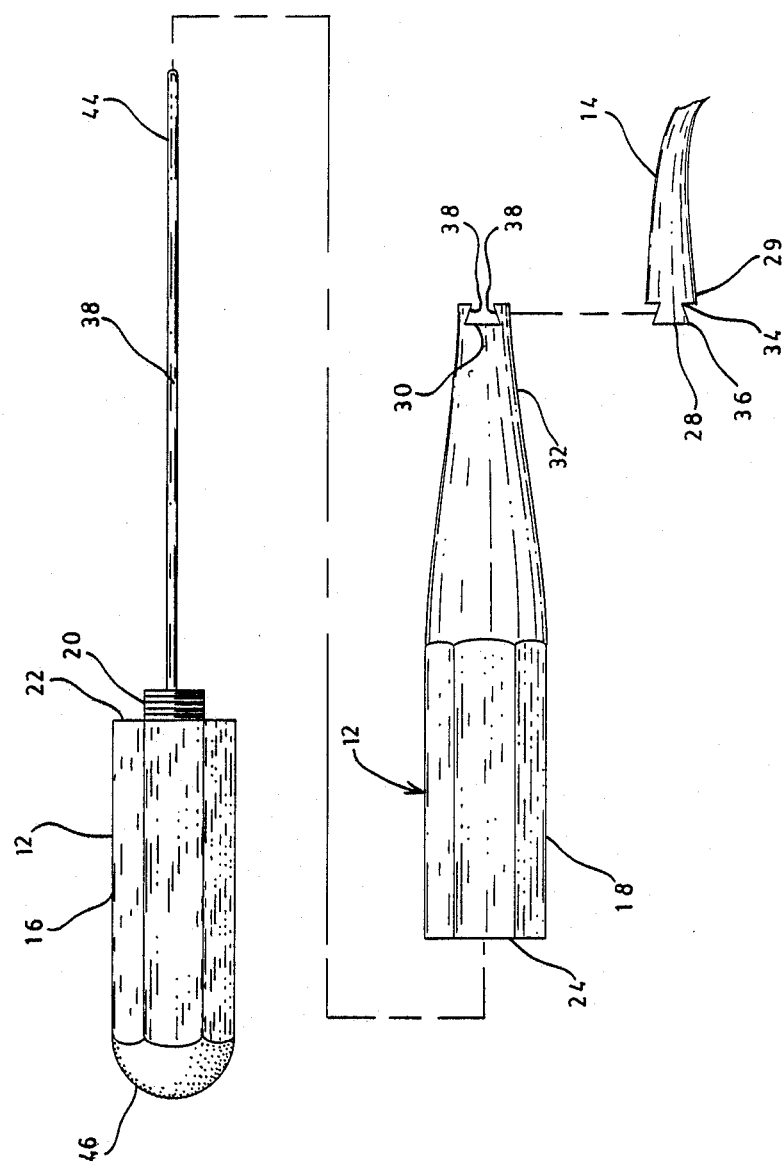
FIG. 3 illustrates an exploded side elevation view of an improved surgical instrument of the present invention.

As illustrated in FIGS. 1 through 3, the handle 12 defines a first or rearward section 16 and a second or forward section 18 with means being provided for releasably joining the sections 16 and 18 in substantially coaxial alignment. More specifically, in the preferred illustrated embodiment, the means for joining the sections 16 and 14 comprise a coaxially oriented threaded protrusion 20 carried by the forward end portion 22 of the rearward section 16 of the handle. Further, the rearward end portion 24 of the forward section 18 of the handle is provided with an axially disposed threaded recess 26 for releasably receiving the threaded protrusion 20, thereby joining the sections 16 and 18.

Of course, the threaded protrusion 20 and registering threaded recess 26 represent only one suitable means for releasably joining the handle sections 16 and 18, and other means can be used as desired. For example, alternate means for releasably joining the sections 16 and 18 are illustrated in FIGS. 7A-C and FIG. 8. Such alternate means comprise a protrusion 21 provided on the rearward end portion 24 of the section 18 which is releasably received in a corresponding recess 23 provided in the forward end portion 22 of the section 16. The protrusion 21 is provided with an L-shaped slot 25 defining a longitudinal leg 31 and a circumferential leg 33. Also, a key member 35 is provided on the interior sidewall of the recess 23. The key member 35 is positioned on the sidewall of the recess 23 such that as the protrusion 21 is inserted into the recess 23, the key member 35 can be slidably received in the longitudinal leg 31 of the slot 25 and rotated into the circumferential leg 33 of the slot 25, thereby releasably locking the sections 16 and 18 together.

Further, in the preferred embodiment, means are provided for releasably locking the key member 35 in the circumferential leg 33 of the slot 25 such that the section 16 does not inadvertently become uncoupled from the section 18 while the instrument 10 is being used. Such means include a radially biasing spring bearing 37 which is received in a longitudially disposed groove 39 provided in the exterior of the protrusion 21. Cooperatively, the recess 23 defines a longitudinally disposed further groove 41 and an adjacent indentation 43. The indentation 43 defines a first longitudinal portion 45 which accommodates the spring bearing 37 as the key member 35 is slidably received in the longitudinal leg 31 of the slot 25. As the key member 35 is rotated into the circumferential leg 33 of the slot 25, the spring bearing follows the indentation toward the further groove 41 thereby engaging the decreasing radius cam surface 47 defined by the indentation 43 adjacent the groove 41. The cam surface 47 serves to radially compress the spring bearing 37 such that the spring bearing 37 rotationally snap fits into the further groove 41 as the key member 35 reaches the desired locking position within the leg 33 of the slot 25. Thus, to uncouple the sections 16 and 18, sufficient rotational disengaging force must be applied to overcome the bias of the spring bearing 37 and snap the spring bearing 37 from the further groove 41.

Each tool member 14 defines a work portion 27 and is provided with a tenon 28 disposed upon its rearward end portion 29 which is closely received in a corresponding mortise 30 provided in the outboard end portion 32 of the forward section 18 of the handle, the mortise 30 being disposed substantially perpendicular to the axis of the handle 12 in the preferred embodiment. More specifically, the tenon 28, when viewed in side elevation as in FIG. 3, defines a narrowed waist portion 34 widening into a rearward expanded portion 36, and, in fact, in the preferred embodiment defines a dovetail tenon. Cooperatively, the mortise 30 is configured to closely receive the tenon 28 both at the waist portion 34 and the expanded portion 36 such that oppositely disposed shoulders 38 are defined. Thus, it will be appreciated by those skilled in the art that as the tenon 28 is received in the mortise 30, axial movement of the tool member 14 relative to the handle 12 is restricted, and, specifically, forward axial movement is prohibited by the shoulders 38 engaging the expanded portion 36 of the tenon 28.

With the axial position of the tool member 14 releasably fixed as described above, means are provided for locking the tenon 28 in position in the mortise 30. In this regard, in the preferred embodiment the rearward section 16 of the handle 12 is provided with a substantially axially disposed locking rod 38 carried by the forward end portion 22 of the section 16. The forward section 18 of the handle 12 defines an axial passageway 40 extending therethrough which is slidably receptive of the locking rod 38. Further, as best illustrated in FIG. 2, each of the tool members 14 defines a locking rod receptor 42 which registers with the passageway 40 as the tenon 32 is seated in the mortise 30 and receives the distal end portion 44 of the locking rod 38. Thus, it will be appreciated by those skilled in the art that in order to releasably secure a tool member 14 to the handle 12, the rearward section 16 of the handle 12 is separated from the forward section 18, and the tenon 28 of the desired tool member 14 is slidably positioned in the mortise 30. The locking rod 38 is then inserted into the passageway 40 and the threaded protrusion 20 threaded into the recess 26. Resultantly, the distal end portion 44 of the locking rod 38 is received in the locking rod receptor 42, prohibiting lateral movement of the tenon 28 within the mortise 30, thereby locking the tool member 14 in place. Of course, to remove a tool member 14, one need only threadably disengage the rearward section 16 of the handle from the section 14 such that the rod 38 is removed from the receptor 42, and slidably remove the tenon 28 from the mortise 30. Of course, it will be appreciated that the rearward section 16 need not be completely disengaged from the forward section 18 in order to unlock the tool member 14. The section 16 need only move rearwardly a sufficient distance to remove the distal end portion 44 of the rod 38 from the rod receptor 42.

It should be noted that it is desirable to have the locking rod receptor 42 extend into the tool member 14 beyond the point to which the distal end portion 44 extends as it is in a locked position. In this regard, on occasion it becomes necessary to strike the handle 12 proximate its rearward end portion 46 in order to communicate the necessary axial force to the tool member 14. Extending the receptor 42 beyond the distal end 44 of the rod 38 ensures that the rod 38 has room to move axially in response to a blow to the rearward end portion 46, such that the distal end 44 is not damaged. Further, it ensures that the force of the blow is evenly transmitted by the sidewalls of the tool member 14.

Figure 6:
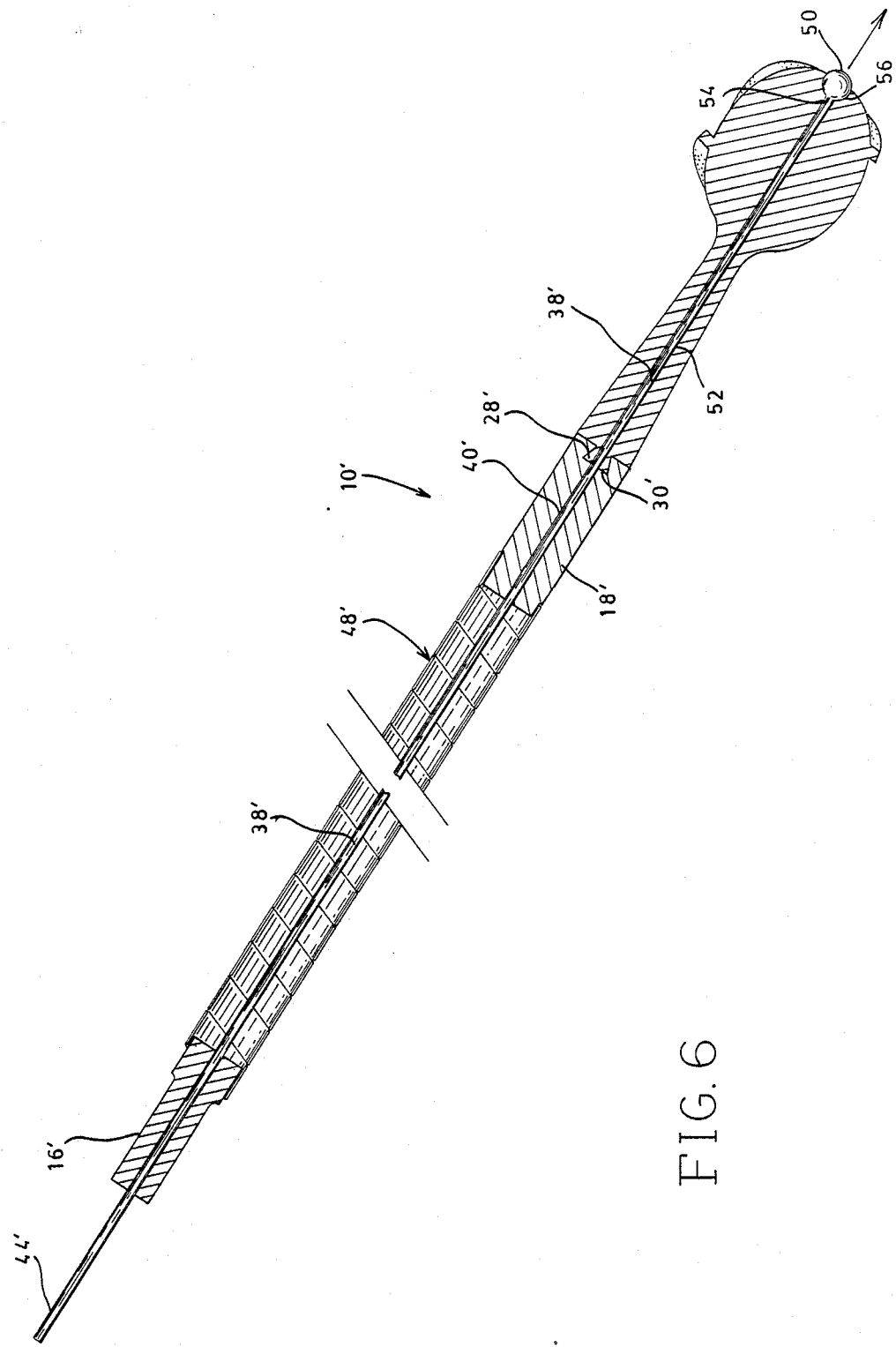
FIG. 6 illustrates a side elevation view, in section, of an alternate embodiment of an improved surgical instrument of the present invention.
Figure 7C:
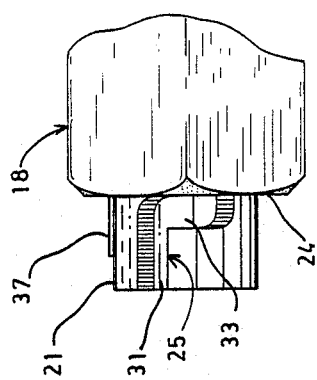
FIG. 7C illustrates a partial side elevation view of the forward section of the tool support member of an improved surgical instrument of the present invention.
Figure 7B:
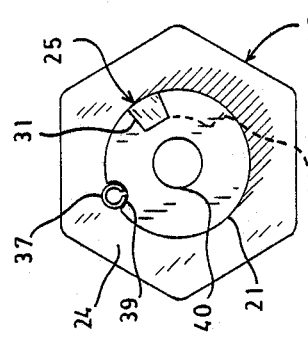
FIG. 7B illustrates a rear view of the forward section of the tool support member of an improved surgical instrument of the present invention.
Figure 8:
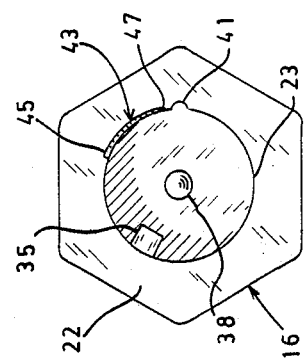
FIG. 8 illustrates a front view of the rearward section of the tool support member of an improved surgical instrument of the present invention.
Figure 7A:
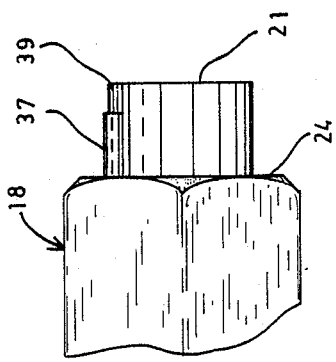
FIG. 7A illustrates a partial side elevation view of the forward section of the tool support member of an improved surgical instrument of the present invention.

In FIGS. 4 through 6, an alternate embodiment of the surgical instrument of the present invention is illustrated at 10'. For the purpose of convenience, features of the instrument 10' which are common to the instrument 10 are referenced by common prime numerals. As illustrated in FIG. 4, the tool support structure of the instrument 10' comprises a flexible shaft 48, and the tool members 14' can define various surgical drill bits, reamers or other surgical tools which require rotation. By way of example, the illustrated tool member 14' defines a reamer of a type used in orthopedic surgery.

The shaft 48 comprises a first rearward section 16' for rotatably engaging a power drive or drill (not shown) and a forward section 18' provided with a mortise 30' for mounting the tool member 14' as described above with respect to the instrument 10. In the preferred illustrated embodiment, the sections 16' and 18' are joined by a flexible sleeve 49. Whereas the shaft 48 can be constructed with a rearward section 16' which carries a locking rod as in the instrument 10 described above, the instrument 10' is provided with an independent locking rod 38' which carries a head portion 50. The tool member 14' is provided with a locking rod receptor passageway 52 extending axially therethrough which registers with the passageway 40' of the shaft 48 as the tenon 28' is in position within the mortise 30'. In order to lock the tool member 14' in place, the distal end portion 44' of the rod 38' is inserted into the passageway 52 via the forward passageway opening 54 to be slidably received in the passageway 40'. (See FIG. 6.) With the rod 38' thusly positioned, lateral position of the tenon 28' in the mortise 30' is fixed.

As illustrated in FIG. 6, an indentation 56 circumscribes the opening 54 in the preferred embodiment. In this regard, the locking rod 38' serves not only as a locking member, but also as a guide for slidably directing the shaft 48 and tool member 14'. Thus, as the shaft and tool member are rotatably moved along the rod 38', the indentation 56 allows the rod 38' to bend without binding at the opening 54 and thereby avoids damage to the rod 38'. Further, when the tool member 14' reaches the distal end of the rod 38', the head portion 50 seats in the indentation 56 such that the functioning of the tool member is not impaired.

It should be noted that with respect to both the surgical instrument 10 and 10', the tenon has been discussed as being carried by the tool member, and the mortise discussed as being defined by the tool support structure. However, it will be understood that with either embodiment, the tenon could be carried by the tool support structure and the operatively associated mortise provided in the tool member.

In light of the above, it will be appreciated that the present invention provides an improved surgical instrument which features detachable tool members. Accordingly, the surgical instrument can be provided with a wide variety of interchangeable tool members defining various work portions or various surgical tasks. Further, worn or defective tool members can be quickly and easily replaced with new tool members without the cost of replacing the entire instrument. Also, the surgical instrument of the present invention requires no wrenches or other tools to accomplish the interchanging of tool members.

While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. An improved surgical instrument, said instrument comprising:

a detachable tool member having an axis, said tool member defining a forward work portion and a rearward end portion, said rearward end portion being provided with a first portion of a tenon/mortise joint for detachably mounting said tool member, said first portion defining a narrowed waist portion and an expanded portion spaced from said waist portion, said tool member being further provided with a locking rod receptor aligned on said axis of said tool member defining an opening in said rearward end portion of said tool member;

an elongated tool support member having a longitudinal axis for detachably engaging said tool member, said tool support member defining an outboard end portion provided with a second portion of said tenon/mortise joint for closely receiving said first portion of said joint on said tool member so as to prohibit axial movement of said tool member relative to said tool support member, said tool support member being further provided with a locking rod passageway along at least a substantial portion of said axis of said support member, said tool support member including a first section having a forward end portion and a second section defining a rearward end portion and said outboard end portion, said tool support member further including means for releasably joining said forward end portion of said first section to said rearward end portion of said second section, said second section defining said locking rod passageway, said passageway extending from said rearward end portion of said second section to said outboard end portion of said second section;

an elongated locking rod for being slidably received in said passageway of said tool support member and in said locking rod receptor of said tool member as the tenon portion of said tenon/mortise joint is positioned within the mortise portion of prohibiting lateral movement of said tenon in said mortise, said elongated locking rod mounted on, and extending outwardly from, said forward end portion of said first section of said tool support member, said locking rod defining a distal end portion for being received in said locking rod receptor of said tool member when said tenon portion is positioned in said mortise portion and said first section and said second section of said support member are joined, whereby lateral movement of said tenon portion in said mortise portion is prohibited; and releasable locking means associated with said locking rod and said tool support member proximate said means for releasably joining said section of said tool support member, and displaced from said tenon/mortise joint, to prevent inadvertent removal of said locking rod from said locking rod receptor of said tool member during use of said surgical instrument.

2. The improved surgical instrument of claim 1 wherein said tenon/mortise joint comprises a dovetail joint.

3. The improved surgical instrument of claim 1 wherein said tool support member defines a handle for grasping and manipulating said surgical instrument.

4. The improved surgical instrument of claim 1 wherein said tool support member defines a flexible shaft for being rotatably received by a power drive.

5. The improved surgical instrument of claim 1 wherein said locking rod receptor defines a further passageway extending through said tool member, said passageway defining a further opening, said further passageway being aligned to register with said passageway of said tool support member as said tenon is positioned in said mortise, said elongated locking rod having a first end portion provided with a head member and a distal end portion, whereby said distal end portion is slidably inserted into said further opening and said rod is received through said further passageway to be received in said passageway of said tool support member as said tenon is positioned in said mortise, thereby prohibiting lateral movement of said tenon in said mortise.

6. The improved surgical instrument of claim 5 wherein said tool support member defines a flexible shaft.

7. The improved surgical instrument of claim 6 wherein said shaft comprises a first section for rotatably engaging a power drive and a second section defining said outboard end portion, said first section and said second section being joined by said flexible sleeve member.

8. The improved surgical instrument of claim 1 wherein said means for releasably joining said forward end portion of said first section to said rearward end portion of said second section comprises a protrusion carried by said rearward end portion of said second section, said protrusion having annular sidewall in which is defined an L-shaped slot defining a longitudinal leg and a circumferential leg, said forward end portion of said first section defining a recess slidably receptive of said protrusion, said recess having interior sidewalls carrying a key member for being received in said recess, whereby said key member is axially received in said longitudinal leg of said slot and rotated into said circumferential leg of said slot to releasably join said first and second sections of said tool support member.

9. The improved surgical instrument of claim 8 wherein said protrusion of said second section of said tool support member is provided with a longitudinally disposed groove for receiving a spring bearing, and wherein said recess of said first section further defines a longitudinally disposed further groove and a longitudinally disposed indentation adjacent said further groove, said indentation defining a first portion for accommodating said spring bearing as said key member is slidably received in said longitudinal leg of said slot, and defines a cam surface adjacent said further groove for radially compressing said spring bearing as said key number is rotated into said circumferential leg of said slot such that said spring bearing snap fits into said further groove whereby said key member is releasably held in said circumferential leg of said slot.

10. The improved surgical instrument of claim 1 wherein said means for releasably joining said forward end portion of said first section to said rearward end portion of said second section comprises an axially disposed threaded protrusion carried by said forward end portion of said first section, and said rearward end portion of said second section defines a threaded recess receptive of said threaded protrusion.

11. An improved surgical instrument with detachable tool member, said instrument comprising:

a tool member having a substantially longitudinal axis, said tool member defining a forward work portion and a rearward end portion, said rearward end portion being provided with a first portion of a tenon/mortise joint for detachably mounting said tool member, said first portion defining a narrowed waist portion and an expanded portion spaced from said waist portion, said rearward end portion of said tool member further defining a locking rod receptor along said axis of said tool member;

a tool support member for detachably engaging said supporting said tool member, said tool support member including a first section having a forward end portion and a second section having a rearward end portion and an outboard end portion, said tool support member further including means for releasably joining said forward end portion of said first section to said rearward end portion of said second section, said outboard end portion of said second section being provided with a second portion of said tenon/mortise joint for closely receiving said first portion of said joint of said tool member, said second section being further provided with a locking rod passageway extending therethrough from said rearward end portion to said outboard end portion, said passageway being aligned to register with said locking rod receptor of said tool member as said tenon is positioned within said mortise;

an elongated locking rod mounted on, and extending outwardly from, said forward end portion of said first section, said locking rod being aligned so as to be slidably received by said passageway of said second section as said first section and said second section are joined, said locking rod defining a distal end portion for being received in said locking rod receptor of said tool member when said tenon/mortise joint portions are interconnected and said first section and said second section are joined, whereby lateral movement of the tenon portion in the mortise portion is prohibited; and releasable locking means associated with said locking rod and said tool support member positioned between said first and second sections of said tool support member.

12. The improved surgical instrument of claim 11 wherein said tool support member defines a handle for grasping and manipulating said surgical instrument.

13. The improved surgical instrument of claim 11 wherein said tool support member defines a flexible shaft for being rotatably received by a power drive.

14. The improved surgical instrument of claim 11 wherein said tenon/mortise comprises a dovetail joint.

15. The improved surgical instrument of claim 11 wherein said means for releasably joining said forward end portion of said first section to said rearward end portion of said second section comprises a protrusion carried by said rearward end portion of said second section, said protrusion having annular sidewalls in which is defined an L-shaped slot defining a longitudinal leg and a circumferential leg, said forward end portion of said first section defining a recess slidably receptive of said protrusion, said recess having interior sidewalls carrying a key member for being received in said recess, whereby key member is axially received in said longitudinal leg of said slot and rotated into said circumferential leg of said slot to releasably join said first and second sections of said tool support member and lock said distal end portion of said locking rod in said locking rod receptor.

16. The improved surgical instrument of claim 15 wherein said protrusion of said second section of said tool support member is provided with a longitudinally disposed groove for receiving a spring bearing, and wherein said recess of said first section further defines a longitudinally disposed further groove and a longitudinally disposed indentation adjacent said further groove, said indentation defining a first portion for accommodating said spring bearing as said key member is slidably received in said longitudinal leg of said slot, and defines a cam surface adjacent said further groove for radially compressing said spring bearing as said key member is rotated into said circumferential leg of said slot such that said spring bearing snap fits into said further groove whereby said key member is releasably held in said circumferential leg of said slot.

17. An improved surgical instrument with detachable tool member, said instrument adapted for complete sterilization, said instrument comprising:
- a tool support member defining an outboard end portion provided with a tenon, said tenon defining a narrowed waist portion and an expanded portion forward of said waist portion, said tool support member having first and second axial sections defining a junction therebetween, said tool support member being further provided with a locking rod passageway defining an opening in said outboard end portion;
- at least one tool member for being detachably mounted on said tool support member, said tool member defining a work portion and a rearward end portion, said rearward end portion being provided with a mortise for closely receiving said tenon of said tool support member, said tool member being further provided with a locking rod receptor defining an opening in said rearward end portion of said tool member;
- an elongated locking rod for being slidably received in said passageway of said tool support member and in said locking rod receptor of said tool member as said tenon is positioned in said mortise for prohibiting lateral movement of said tenon in said mortise; and
- means at said junction between said first and second sections of said tool support member for releasably joining said sections and for releasably locking said locking rod in said locking rod receptor, said means including a protrusion carried by a confronting portion of one of said sections, said protrusion having an annular sidewall provided with an L-shaped slot defining a longitudinal leg and circumferential leg, said confronting portion of the other section of said tool support member provided with a recess receptive of said protrusion, said recess having a interior sidewall carrying a key member for being received in said recess, whereby said key member is axially received in said longitudinal leg of said slot when said first and second sections are joined, with said key member being rotated into said circumferential leg to releasably join said first and second sections of said tool support member and releasably lock said locking rod in said locking rod receptor of said tool member.

18. The improved surgical instrument of claim 17 wherein said protrusion of said second section of said tool support member is provided with a longitudinally disposed groove for receiving a spring lift bearing, and wherein said recess of said first section further defines a longitudinally disposed further groove and a longitudinally disposed indentation adjacent said further groove, said indentation defining a first portion for accommodating said spring bearing as said key member is slidably received in said longitudinal leg of said slot, and defines a cam surface adjacent said further groove for radially compressing said spring bearing as said key member is rotated into said circumferential leg of said slot such that said spring bearing snap fits into said further groove whereby said key member is releasably held in said circumferential leg of said slot.

* * * * *